US006283918B1

United States Patent
Kanda et al.

(10) Patent No.: US 6,283,918 B1
(45) Date of Patent: Sep. 4, 2001

(54) MEDICAL IMAGE DIAGNOSTIC APPARATUS

(75) Inventors: Ryoichi Kanda, Otawara; Kazuhiro Iinuma, Tochigi-ken; Shinichi Hashimoto, Otawara, all of (JP)

(73) Assignee: Kabushiki Kaisha Toshiba, Kawasaki (JP)

( * ) Notice: Subject to any disclaimer, the term of this patent is extended or adjusted under 35 U.S.C. 154(b) by 0 days.

(21) Appl. No.: 09/163,976

(22) Filed: Sep. 30, 1998

(30) Foreign Application Priority Data

Sep. 30, 1997 (JP) .................................................. 9-265661
Sep. 29, 1998 (JP) ................................................. 10-275354

(51) Int. Cl.$^7$ ...................................................... A61B 8/00
(52) U.S. Cl. .......................... 600/441; 128/916; 600/454
(58) Field of Search ..................................... 600/425, 440, 600/441, 443, 410, 419, 454; 128/916, 920; 382/128

(56) References Cited

U.S. PATENT DOCUMENTS

| 5,720,291 | | 2/1998 | Schwartz . |
| 5,865,750 | * | 2/1999 | Hatfield et al. . |
| 5,879,302 | * | 3/1999 | Hashimoto et al. . |
| 5,899,863 | * | 5/1999 | Hatfield et al. . |
| 5,904,653 | * | 5/1999 | Hatfield et al. . |
| 5,911,691 | * | 6/1999 | Mochizuki et al. . |
| 5,928,151 | * | 7/1999 | Hossack et al. . |
| 5,931,784 | * | 8/1999 | Kajiwara et al. . |
| 5,954,653 | * | 9/1999 | Hatfield et al. . |
| 6,014,473 | * | 1/2000 | Hossack et al. . |
| 6,048,312 | * | 4/2000 | Ishrak et al. . |

* cited by examiner

Primary Examiner—Marvin M. Lateef
Assistant Examiner—Shawna J Shaw
(74) Attorney, Agent, or Firm—Oblon, Spivak, McClelland, Maier & Neustadt, P.C.

(57) ABSTRACT

A parenchymatous tissue image and a blood vessel image are synthesized as follows. First, a tomographic image of a specific cross section of the parenchymatous tissue image is synthesized with the blood vessel image closer to the viewpoint along the Z-axis than the tomographic image. Then, the resulting image is displayed. Thereafter, the operator inputs specific data from operation unit including a mouse and a keyboard, thereby changing the position of a displayed tomographic image along the Z-axis. This enables the operator to sequentially display two-dimensional tomographic images (B-mode images) constituting a three-dimensional parenchymatous tissue image as if to turn over the pages of a book.

23 Claims, 12 Drawing Sheets

REGION SETTING INFORMATION

×---× TRACING CURVE DURING TRACING WORK

FIG. 11

$DP = \iiint_R d(x, y, z) \, dxdydz$

DP: TOTAL OF POWER OF DOPPLER SIGNAL IN TUMOR
d: POWER OF DOPPLER SIGNAL AT EACH POINT
R: DOMAIN OF INTEGRATION (VOLUME OF TUMOR)

$BP = \iiint_R B(x, y, z) \, dxdydz$

BP: TOTAL OF POWER OF B-MODE SIGNAL IN TUMOR
d: POWER OF B-MODE SIGNAL AT EACH POINT
R: DOMAIN OF INTEGRATION (VOLUME OF TUMOR)

VASCULARITY INDEX = f(DP, BP)    FOR EXAMPLE, f(DP, BP) = DP/BP

MEDICAL IMAGE DIAGNOSTIC APPARATUS

BACKGROUND OF THE INVENTION

This invention relates to a three-dimensional display of medical images, and more particularly to a medical image diagnostic apparatus which provides images representing tissues forming internal organs in a living organism and those representing structures, such as blood vessels, in an easy-to-understand form suitable for diagnosis or medical treatment and to a medical image diagnostic apparatus which obtains quantitative parameters for a living organism on the basis of three-dimensional medical images.

In various diagnoses, it is important to grasp the vascular architecture in a living organism three-dimensionally. For instance, to grasp the nutritive blood vessels entering the hepatophyma in the lever is important in distinguishing between a malignant tumor and a benign tumor or judging the effect of treatment. When the renal function is evaluated, the state of the return of bloodstream in the kidney serves as an index.

Only three-dimensional information on the vascular architecture is often not enough to make an appropriate diagnosis. For instance, even when blood vessels are sensed and visualized near the hepatophyma and a three-dimensional image of the blood vessels is obtained, it is necessary to know whether the blood vessels have gone into the tumor to determine whether the blood vessels in the tumor are nutritive ones. When the image of the tumor is obtained only from the image of the blood vessels, the position of the tumor cannot be located, preventing diagnosis. Furthermore, it is not clear whether the bloodstream has flown back close to the surface of the kidney, unless it is known where the parenchyma or surface of the kidney is. That is, sufficient diagnosis cannot be made unless an image of parenchymatous internal organs whose positional relationship with an image of the bloodstream or the blood vessels is kept unchanged is obtained and displayed simultaneously.

In recent years, it has been getting important to quantitatively represent the amount of bloodstream and the abundance of blood vessels. The prior art, however, has encountered the problem of being unable to determine not only the calculation range of quantitative parameters from only an image of blood vessels but also quantitative parameters with sufficient reliability. It also has encountered the problem of having difficulty in determining sufficiently quantitative parameters.

BRIEF SUMMARY OF THE INVENTION

It is, accordingly, an object of the present invention to overcome the problems by providing a medical image diagnostic apparatus which displays an image of a network structure, such as blood vessels, and an image of tissue with gradation, such as parenchymatous internal organs, in such a manner that their positional relationship can be observed accurately.

Another object of the present invention is to provide a medical image diagnostic apparatus capable of obtaining quantitative parameters accurately from three-dimensional information on an image of tissue and on an image of a structure, such as blood vessels.

The foregoing objects are accomplished by providing the following medical image diagnostic apparatus.

A medical image diagnostic apparatus acquires three-dimensional information from a structure, such as a blood vessel, and three-dimensional information from a tissue, such as a parenchymatous internal organ, in different imaging modes in such a manner that the positional relationship between the two types of three-dimensional information is kept unchanged.

Furthermore, the apparatus is characterized by:

(1) displaying a cross-sectional image of a tissue image and a three-dimensional image of a structure on the same screen in such a manner that the coordinates of the cross-sectional image correspond to those of the three-dimensional image and changing the display area of the three-dimensional image in front of or behind the cross-sectional image.

(2) specifying a region from which parameters are to be obtained for the three-dimensional data on the tissue image in obtaining quantitative parameters for the structure and determining the quantitative parameters from the three-dimensional information on the structure image corresponding to the specified region.

(3) using both information on the tissue image and information on the structure image not only to set the region but also calculate the quantitative parameters.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The file of this patent contains at least one color photograph executed in color. Copies of this patent with color photographs will be provided by the Patent and Trademark Office upon request and payment of the necessary fee.

The accompanying drawings, which are incorporated in and constitute a part of the specification, illustrate presently preferred embodiments of the invention, and together with the general description given above and the detailed description of the preferred embodiments give below, serve to explain the principles of the invention.

DETAILED DESCRIPTION OF THE INVENTION

Hereinafter, referring to the accompanying drawings, embodiments of the present invention will be explained.

Embodiments of an image diagnostic instrument capable of simultaneously acquiring information on internal organs' parenchyma and information on structures, such as blood vessels, include an ultrasound diagnostic apparatus, an X-ray computed tomography apparatus (CT), and an magnetic resonance imaging apparatus (MRI).

In a first to a fourth embodiment of the present invention which will be explained below, the invention is applied to an ultrasound diagnostic apparatus. With an ultrasound diagnostic apparatus, a tissue image of internal organs' parenchyma is obtained in a B-mode imaging (a first imaging mode) and a structure image (a blood vessel image) at almost the same time is obtained in a color Doppler mode (a second imaging mode). The positional coordinates of the B-mode image correspond to those of the color Doppler image. Three-dimensional data items (volume data items) in both of the modes can be obtained almost at the same time by mechanically or manually moving a one-dimensional array ultrasonic probe in such a manner that the probe fans out or by using a two-dimensional array ultrasonic probe. Of course, the spatial positional coordinates of the volume data items in both of the imaging modes correspond to each other.

The pieces of information acquired in the color Doppler mode basically include two types of information made up of the speed of bloodstream and the power of the reflected signal from the bloodstream. The power information, however, is more suitable for constructing a blood vessel image than the bloodstream information. While in the first to fourth embodiments, images are based on the power information, they may be based on the speed information or other suitable information.

For example, in recent years, there has been proposed a method of visualizing a blood vessel image or the perfusion in internal organs' parenchyma using a contrast agent. The method includes a contrast echo method and an imaging method known as a harmonic imaging method or a flash echo imaging method. The present invention can be practiced even when the imaging methods are applied.

As described above, with the present invention, image data items (three-dimensional data items at least in one mode) are acquired in each of the imaging modes in such a manner that the positional coordinates in one mode correspond to those in the other mode. Then, the data items in one mode are distinguished from those in the other mode, and they are stored in storage means, such as an image memory, so as to enable subsequent processing.

(First Embodiment)

An ultrasound diagnostic apparatus according to a first embodiment of the present invention displays a cross section of a specified region or two-dimensional tomographic images of cross sections in the form of tissue images. The apparatus constructs three-dimensional structure image on the basis of acquired data items in the imaging mode different from that of the tissue images, synthesizes it with a tissue image, and displays the resulting image.

Figure 1:
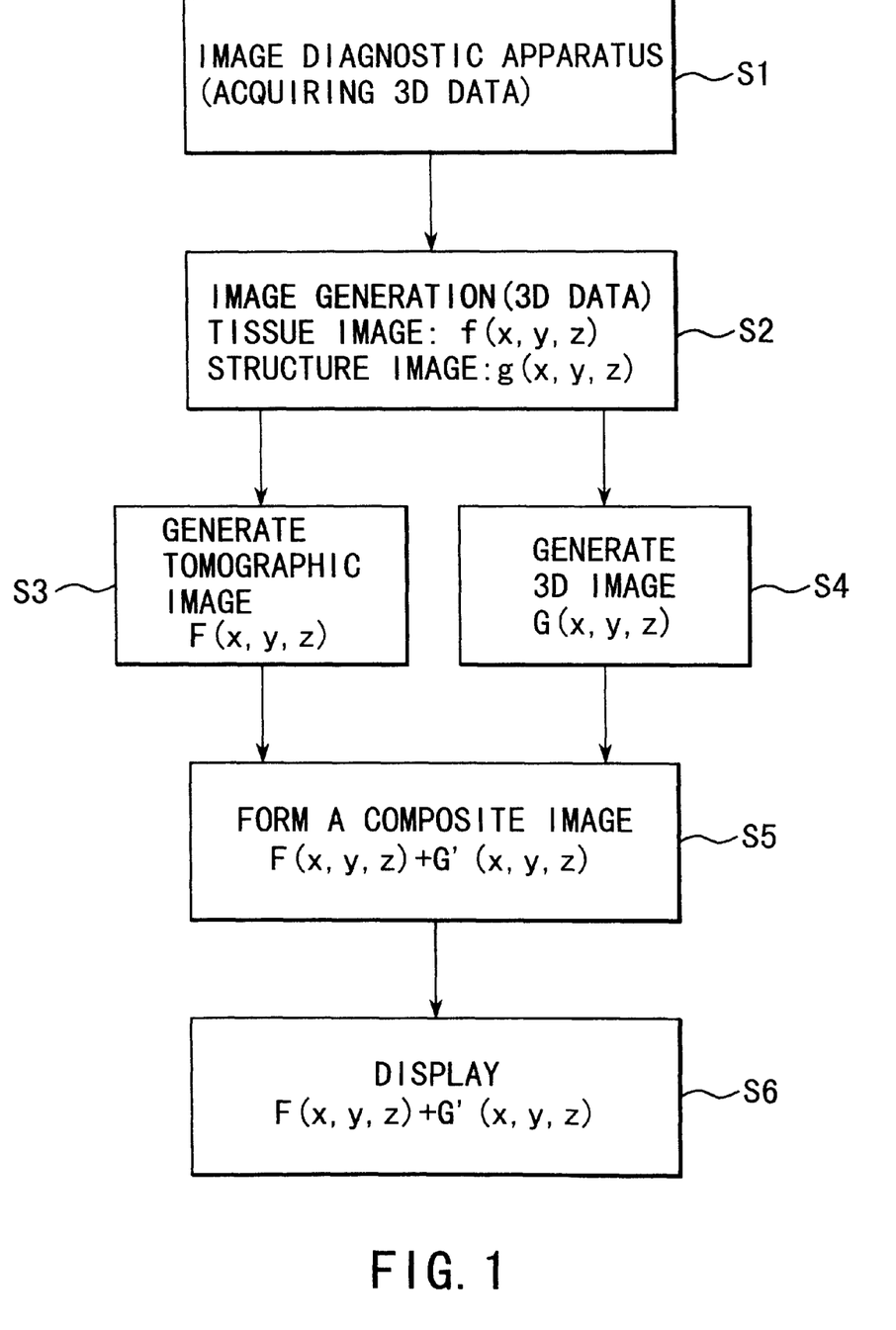
FIG. 1 is a flowchart covering the process of acquiring three-dimensional data items to the process of synthesizing images in an ultrasonic diagnostic apparatus according to a first embodiment of the present invention.

FIG. 1 is a flowchart covering the processes of acquiring tissue images and structure images and synthesizing them to the process of displaying the resulting image in an ultrasonic diagnostic apparatus according to a first embodiment of a medical image diagnostic apparatus of the present invention.

First, as shown in step S1, three-dimensional data items are acquired using the ultrasound diagnostic apparatus. The acquisition is effected in two types of imaging mode: a B mode and a color Doppler mode. B-mode three-dimensional data items and color-Doppler-mode three-dimensional data items are acquired in the respective modes.

Next, at step S2, on the basis of the acquired three-dimensional data, two types of images, tissue images (f(x, y, z): monochrome gradation images) and structure images (g(x, y, z): color images), are generated.

Then, at step S3, on the basis of the tissue images, cross-sectional transforming and image processing, such as texture mapping, are effected to generate a tomographic image F(x, y, z). At step S4, on the basis of the structure images, a three-dimensional (3D) image G(x, y, z) is generated.

At step S5, G'(x, y, z) is obtained by setting a suitable transmittance parameter for the 3-D image G(x, y, z) and effecting image processing, such as volume rendering, or by cutting out data on a specific portion of the 3-D image G(x, y, z) and effecting image processing, such as volume rendering. Thereafter, a tomographic image F(x, y, z) and the 3-D image G'(x, y, z) after image processing are synthesized to produce a composite image F(x, y, z)+G'(x, y, z). Then, at step S6, the composite image F(x, y, z)+G'(x, y, z) is displayed.

The generation and display of an image at step S3 to step S5 will be explained concretely.

FIG. 2 shows a basic concept of the display method in the first embodiment. It illustrates how a parenchymatous tissue image and a blood vessel image (a structure image) in an a region including a tumor are synthesized and the resulting image is displayed. FIG. 2A shows a parenchymatous tissue image. A dotted line in the parenchymatous tissue image T represents, for example, a spherical tumor Tt. All of the parenchymatous tissue image T is composed of two-dimensional tomographic images. FIG. 2B shows a structure image (in this case, a blood vessel image).

Figure 2A:
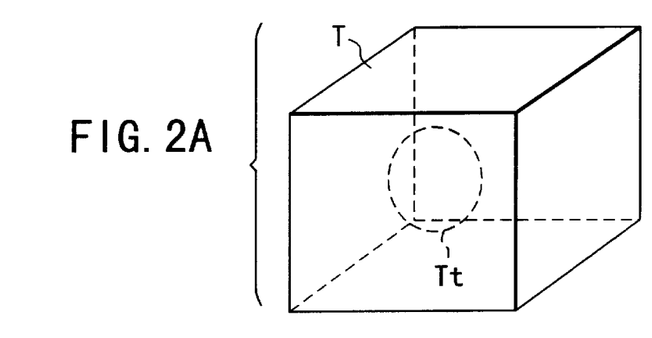
FIG. 2A is a drawing to help explain the process of synthesizing a tissue image including a tumor and a blood vessel image and displaying the resulting image and shows a parenchymatous tissue image.
Figure 2B:
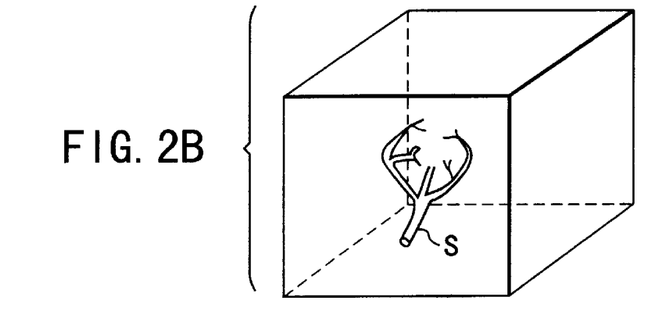
FIG. 2B is a drawing to help explain the process of synthesizing a tissue image including a tumor and a blood vessel image and displaying the resulting image and shows a structure image (blood vessel image)

The parenchymatous tissue image T and blood vessel image S shown respectively in FIGS. 2A and 2B are synthesizied and displayed as follows.

Figure 2C:
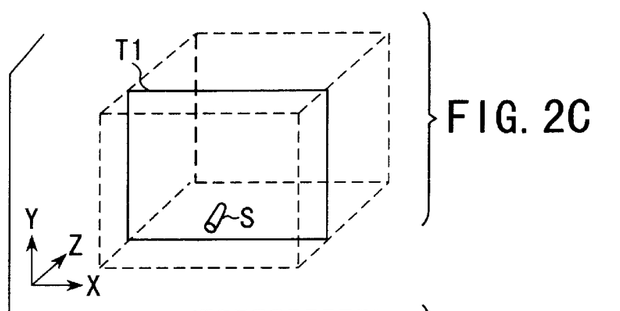
FIG. 2C is a drawing to help explain the process of synthesizing a tissue image including a tumor and a blood vessel image and displaying the resulting image as a first representation.

First, as shown in FIG. 2C, a two-dimensional tomographic image T1 of a specific cross section (the XY plane in the initial position on the Z-axis) of the parenchymatous tissue image T and the 3-D image S of the blood vessel concerning a portion closer to the viewpoint along the Z-axis than the tomographic image T1 are synthesized and the resulting image is displayed. At this point, a 3-D image of blood vessels in the portion behind the tomographic image T1 is not displayed.

The operator can change the position of the displayed tomographic image along the Z-axis by inputting specific data from operation means, such as a mouse or a keyboard. This enables the operator to display two-dimensional tomographic images (B-mode images) constituting a three-dimensional parenchymatous tissue image one after another as if to turn over the pages of a book.

Figure 2D:
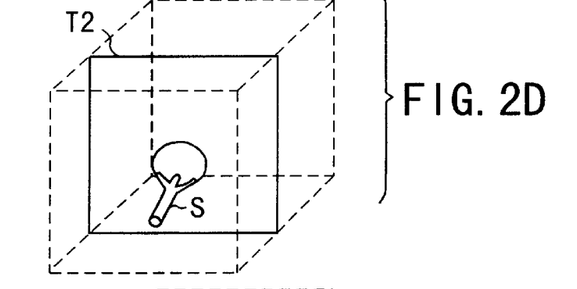
FIG. 2D is a drawing to help explain the process of synthesizing a tissue image including a tumor and a blood vessel image and displaying the resulting image as a second representation.
Figure 2E:
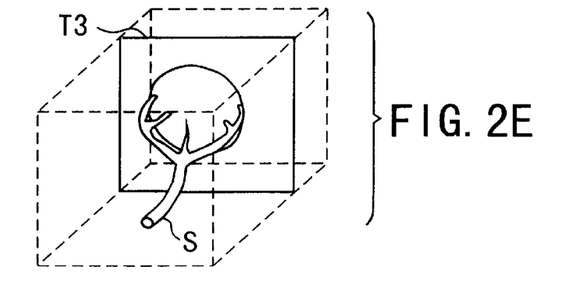
FIG. 2E is a drawing to help explain the process of synthesizing a tissue image including a tumor and a blood vessel image and displaying the resulting image as a third representation.

FIG. 2D shows a tomographic image T2 when its position on the Z-axis has been moved farther back from T1 with the operation means. FIG. 2E shows a tomographic image T3 when its position on the Z-axis has been moved farther back from T2 with the operation means.

As a result of updating the display from the tomographic image T1 to the image T3 with the operation means, the representation of the blood vessel image S is also updated automatically as shown in FIGS. 2C to 2E.

Consequently, the operator can change the display area of the 3-D image of blood vessels by changing the display position of the tomographic image (or manipulates the display area). Repeating the area manipulation, the operator can observe the positional relationship between the tumor represented by the tissue image and the blood vessels (image) accurately.

Figure 3:
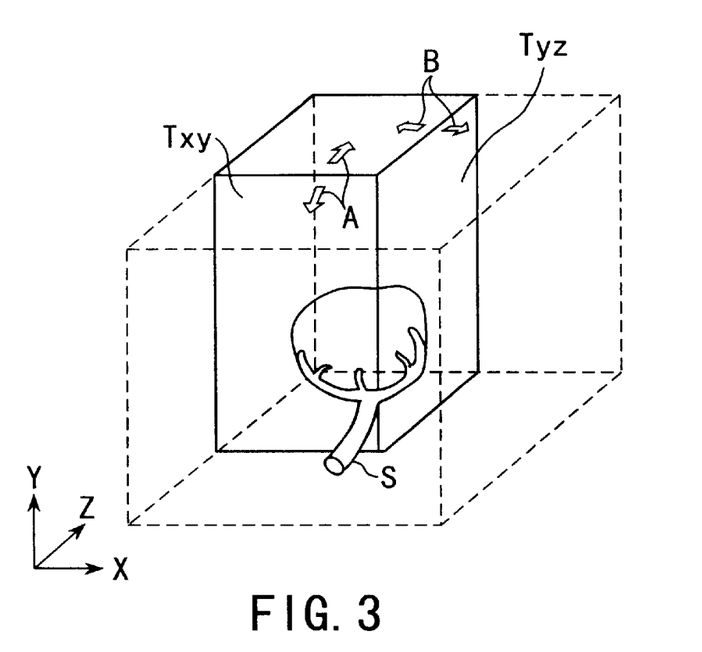
FIG. 3 shows how the display area of a blood vessel image is changed by changing the display position of a tomographic image.

FIG. 3 shows another example of the display area manipulation. While in the example of FIG. 2, only the tomographic image in the XY plane has been displayed, not only a tomographic image Txy in the XY plane but also a tomographic image Tyz in the YZ plane is also displayed in the example of FIG. 3. Although in the example of FIG. 2, the display position of the tissue image has been changed in the direction of Z, not only the position in the direction of Z (in the direction of arrow A) of the tomographic image Txy but also the position in the direction of X (in the direction of arrow B) of the tomographic image Tyz can be changed with the operation means and the display area of the tissue image can be changed in many directions in the example of FIG. 3. Of course, the display area may be changed into any form.

Figure 4:
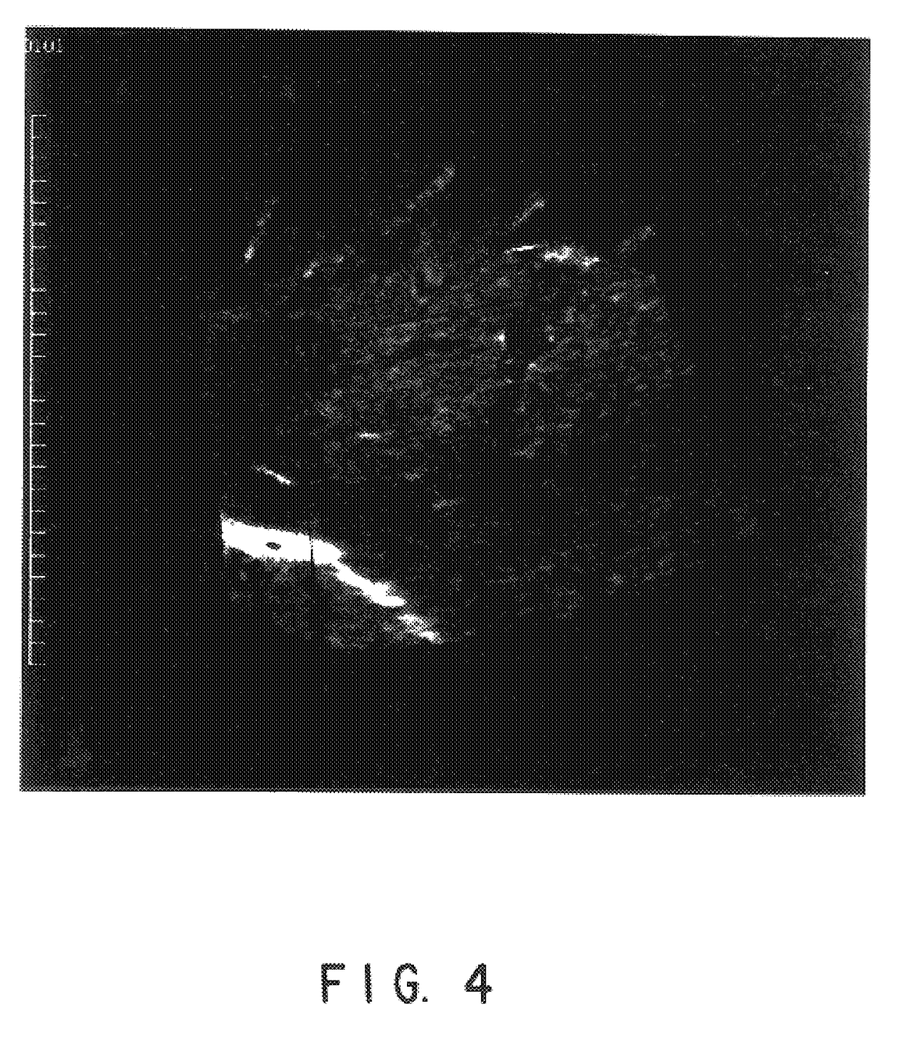
FIG. 4 is a color photograph of a concrete example showing how the display area of a blood vessel image is changed by changing the display position of a tomographic image.

FIG. 4 is a color photograph showing a concrete example of changing the display area of a blood vessel image by changing the display position of its tomographic image.

Figure 5:
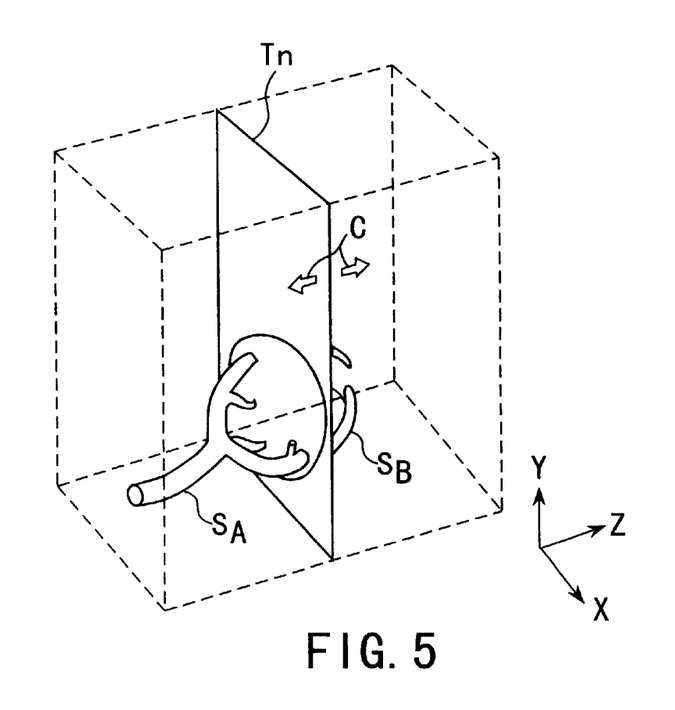
FIG. 5 shows an example of a synthesized representation when the X-axis, Y-axis, and Z-axis are rotated through a specific angle.

FIG. 5 illustrates an example of a composite display when the X-axis, Y-axis, and Z-axis are rotated through a specific angle. In this example, not only the base end Sa of the blood vessel structure but also the tip end Sb are displayed. The position of a tomographic image Tn can be changed in the direction of Z or in the direction of arrow C.

Figure 6:
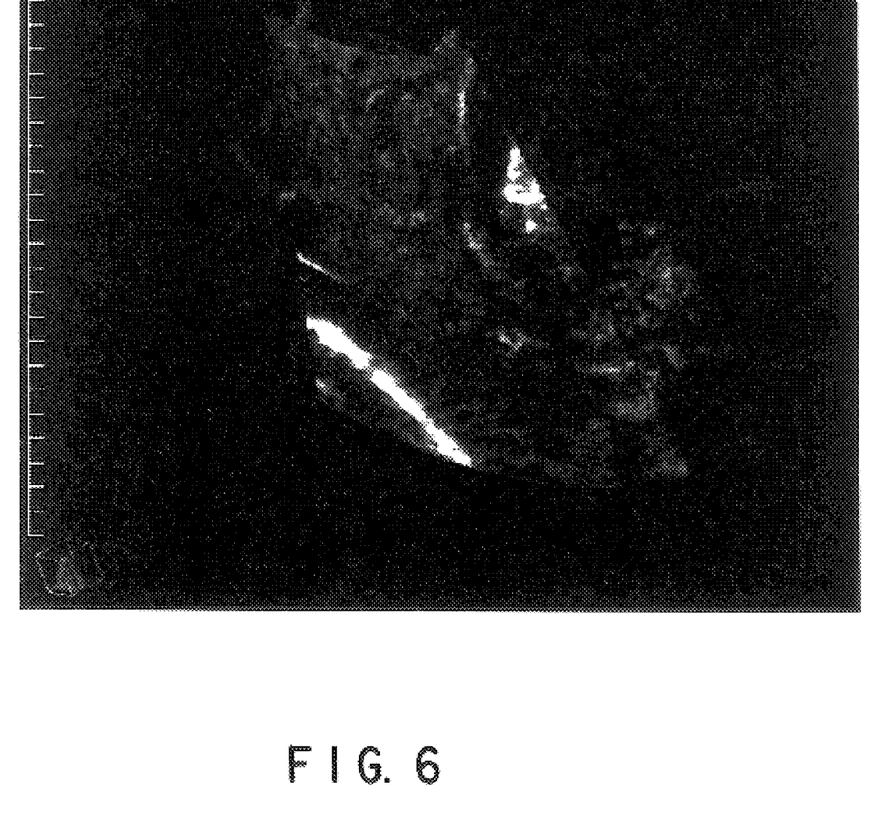
FIG. 6 is a color photograph showing an example of a synthesized representation when the X-axis, Y-axis, and Z-axis are rotated through a specific angle.

FIG. 6 is a color photograph showing a concrete example of displaying not only the base end of the blood vessel structure but also its tip end.

Figure 7:
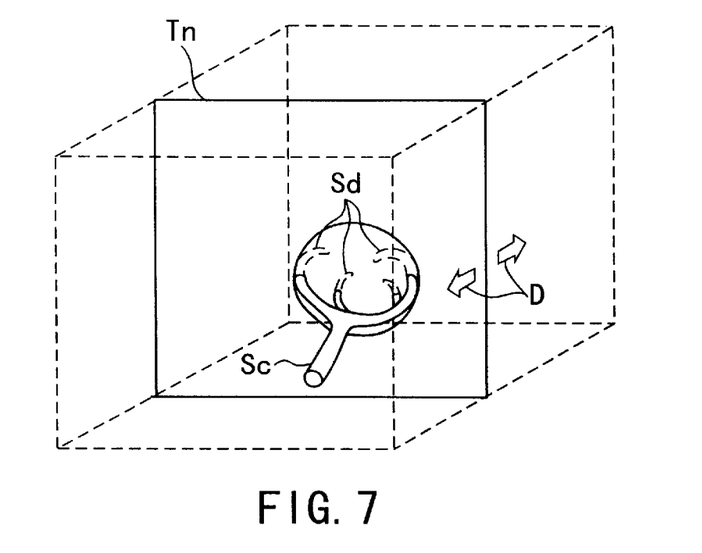
FIG. 7 shows an example of a synthesized representation when a blood vessel image hid behind the display area of a tissue image is displayed so as to be seen through the tissue image.

FIG. 7 shows an example of a representation when a blood vessel image hid behind the display area of a tissue image is displayed so as to be seen through the tissue image. In this example, not only the base end Sc of a blood vessel structure is displayed three-dimensionally, but also a blood vessel image Sd closer to the tip end than the position of the tomographic image Tn is displayed so as to be seen through the tomographic image Tn. This is achieved by changing the transmittance of the tomographic image Tn.

Figure 8:
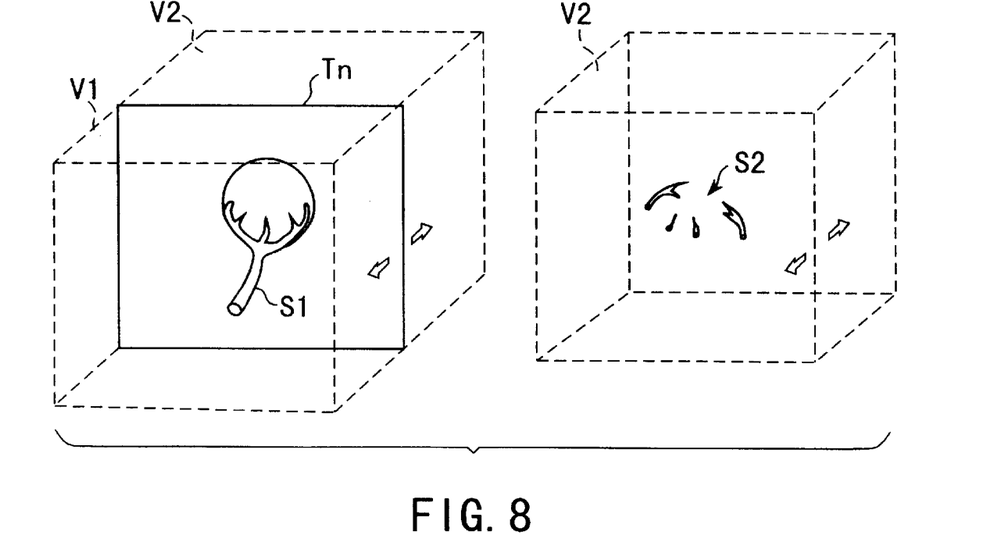
FIG. 8 shows two three-dimensional images displayed side by side.

FIG. 8 shows two three-dimensional images displayed side by side. In this example, in three-dimensional display areas V1 and V2 divided by the tomographic image Tn, a blood vessel image S1 in area V1 (on the viewpoint side) and a blood vessel image S2 in area V2 (farther back from the tomographic image Tn) are displayed side by side.

With the display method as described above, the operator can grasp the positional relationship between the tissue image and the structure from various angles accurately. Furthermore, being able to change not only the area and cross section of the tissue image but also the direction of the viewpoint simultaneously, the operator can make a closer observation.

(Second Embodiment)

When an index (e.g., a quantitative parameter) for indicating the abundance of tumor nutritive blood vessels are obtained from the acquired 3-D information, it is very important how to determine the range of index.

FIG. 9 is a drawing to help explain an example of a method of setting the range using structure images related to the present embodiment. As shown in FIG. 9A, consideration will be given to a case where many blood vessels different from the nutritive blood vessels to the tumor run near the tumor. It is difficult to judge the blood vessels one by one on the basis of the blood vessel image. In contrast, from the tissue image, the extent of a tumor can be determined accurately. Therefore, in the second embodiment, a range for quantification is determined on the basis of a tissue image (FIG. 9B). Specifically, in the second embodiment, as shown in FIGS. 9C to 9E, not only parenchymatous tissue images in planes in three directions (in this case, a specific XY plane (FIG. 9C), YX plane (FIG. 9D), and XZ plane (FIG. 9E)) are displayed, but also a range for quantification is to be set by tracing a tumor on these images. In FIGS. 9C to 9E, hatching indicates a tumor and doted lines represent the set range.

Figure 9A:
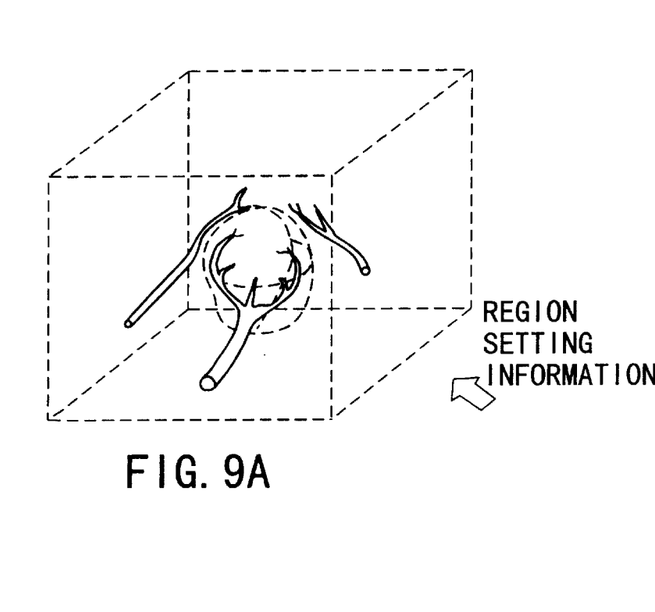
FIG. 9A is a drawing to help explain an example of a method of setting a range using a tissue image in an ultrasound diagnostic apparatus according to a second embodiment of the present invention and shows a structure image.
Figure 9B:
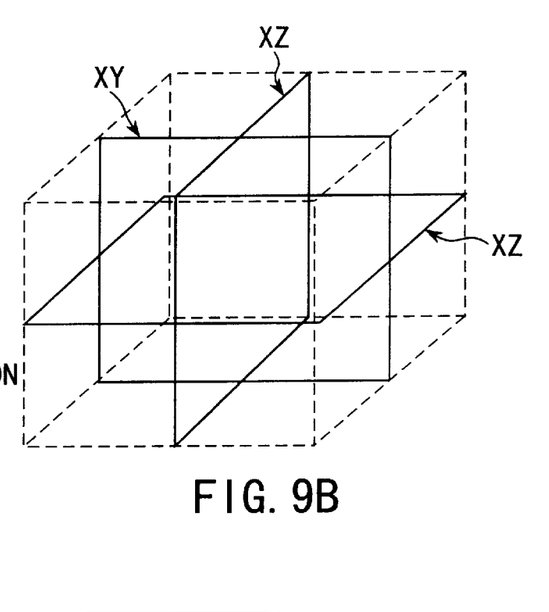
FIG. 9B is a drawing to help explain an example of the method of setting the range and shows a parenchymatous tissue image.
Figure 9C:
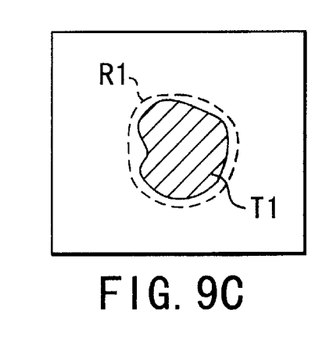
FIG. 9C is a drawing to help explain an example of the method of setting the range and shows an image in the XY plane.
Figure 9D:
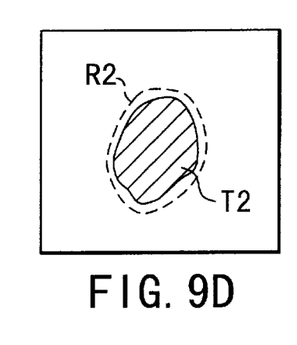
FIG. 9D is a drawing to help explain an example of the method of setting the range and shows an image in the YZ plane.
Figure 9E:
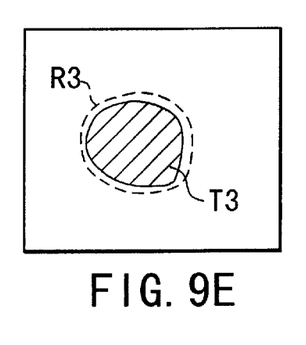
FIG. 9E is a drawing to help explain an example of the method of setting the range and shows an image in the ZX plane.

More specifically, range setting information R1 is obtained by tracing a cross section T1 of the tumor on the tissue image in the XY plane; range setting information R2 is obtained by tracing the cross section T1 of the tumor on the tissue image in the XZ plane; and range setting information R3 is obtained by tracing a cross section T3 of the tumor on the tissue image in the XZ plane.

Although such tracing work is needed, the quantitative parameters can be obtained under the precise definition in the second embodiment.

Figure 10:
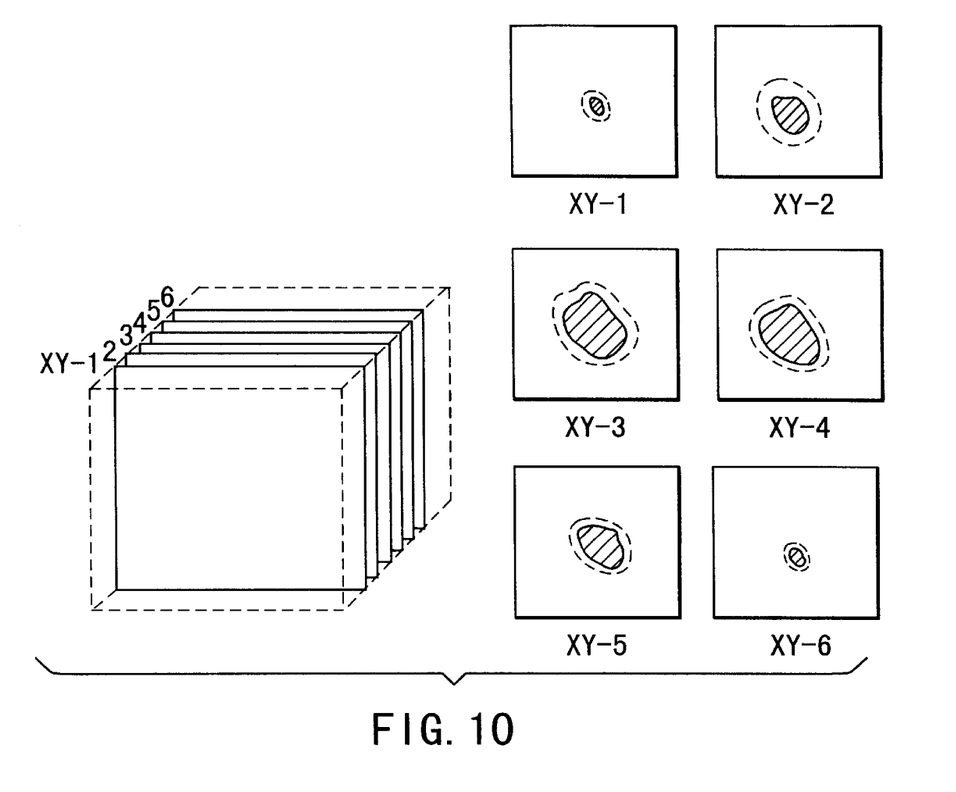
FIG. 10 shows another example of tracing a tissue image.

FIG. 10 shows another example of tracing the tissue image as in FIG. 9. In this example, tracing planes are chosen from cross sections XY-1 to XY-6 of a parenchymatous tissue image parallel to each other as shown in FIG. 10. FIG. 10 shows tracing plane XY-1 to tracing plane XY-6.

Figure 11:
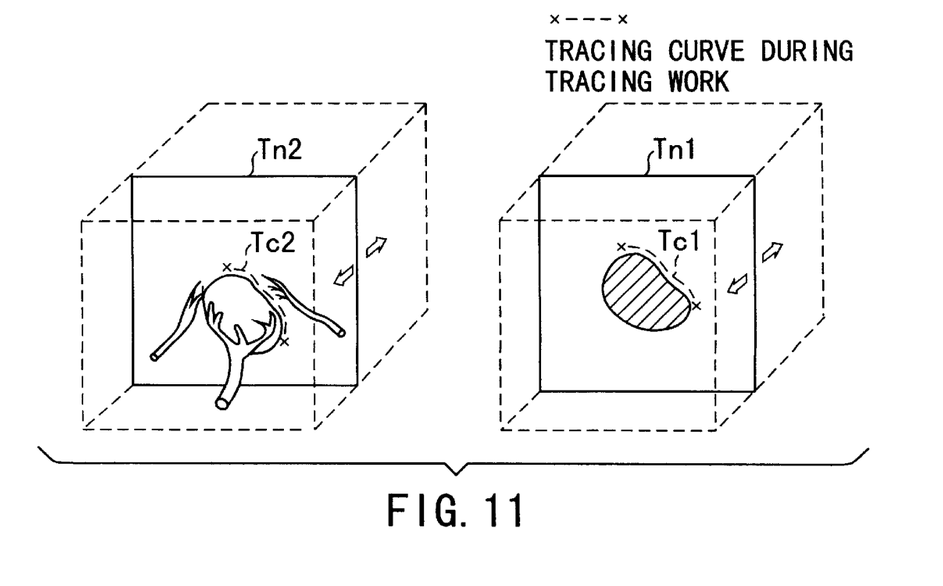
FIG. 11 shows an example of displaying a tracing curve also on a composite image of a blood vessel image and a tissue image in tracing the tissue image.

FIG. 11 shows an example of displaying a tracing curve also on a composite image of a blood vessel image and a tissue image in tracing the tissue image. In this example, a tracing curve Tc1 (X ----- X) is displayed on a tissue image Tn1 to be traced and a tracing curve Tc2 corresponding to Tc1 is displayed on a composite image of a blood vessel image S and a tissue image Tn2.

This enables the operator to do tracing work while making sure that the other blood vessels are outside the tracing range. Therefore, the operator need not worry much about the accuracy of tracing and can do tracing easily and reliably. The tracing curves may be displayed on the blood vessel image, not on the composite image of the blood vessel image and tissue image.

In both examples in FIG. 10 and FIG. 11, images of cross sections to be traced may be only the images of tissues or those of two-dimensional composite images obtained by superposing the blood vessel image of the same cross section on the tissue tomographic image.

Tracing is not necessarily done manually by the operator. It may be done automatically using a suitable algorithm.

As described above, with the second embodiment, a range for computing quantitative parameters can be set easily and accurately.

(Third Embodiment)

When quantitative parameters are used, using only information on the structure may cause a quantification problem. The third embodiment provides information on higher quantification by using also information on tissue images.

For example, in color Doppler power display with an ultrasound diagnostic apparatus, the abundance of bloodstream in a tumor, or vascularity, is quantified from the total of the Doppler power values in the tumor. In this case, a hindrance to quantification is the fact that the Doppler power itself is influenced by the apparatus or the characteristic of a living organism. Specifically, when the transmission power or reception sensitivity of the apparatus is low, even if the vascularity of the tumor is high, the Doppler power obtained from the tumor will be low. Moreover, when a tumor is in a deep position, because sound waves attenuate in the course of traveling between the ultrasonic probe and the tumor, the Doppler signal also attenuates. These become the factors that degrade the quantification based on the Doppler signal seriously.

The change of the Doppler signal caused by the factors similarly acts on tissue images. Therefore, in the third embodiment, correction is made using the signal from a tissue image.

Figure 12:
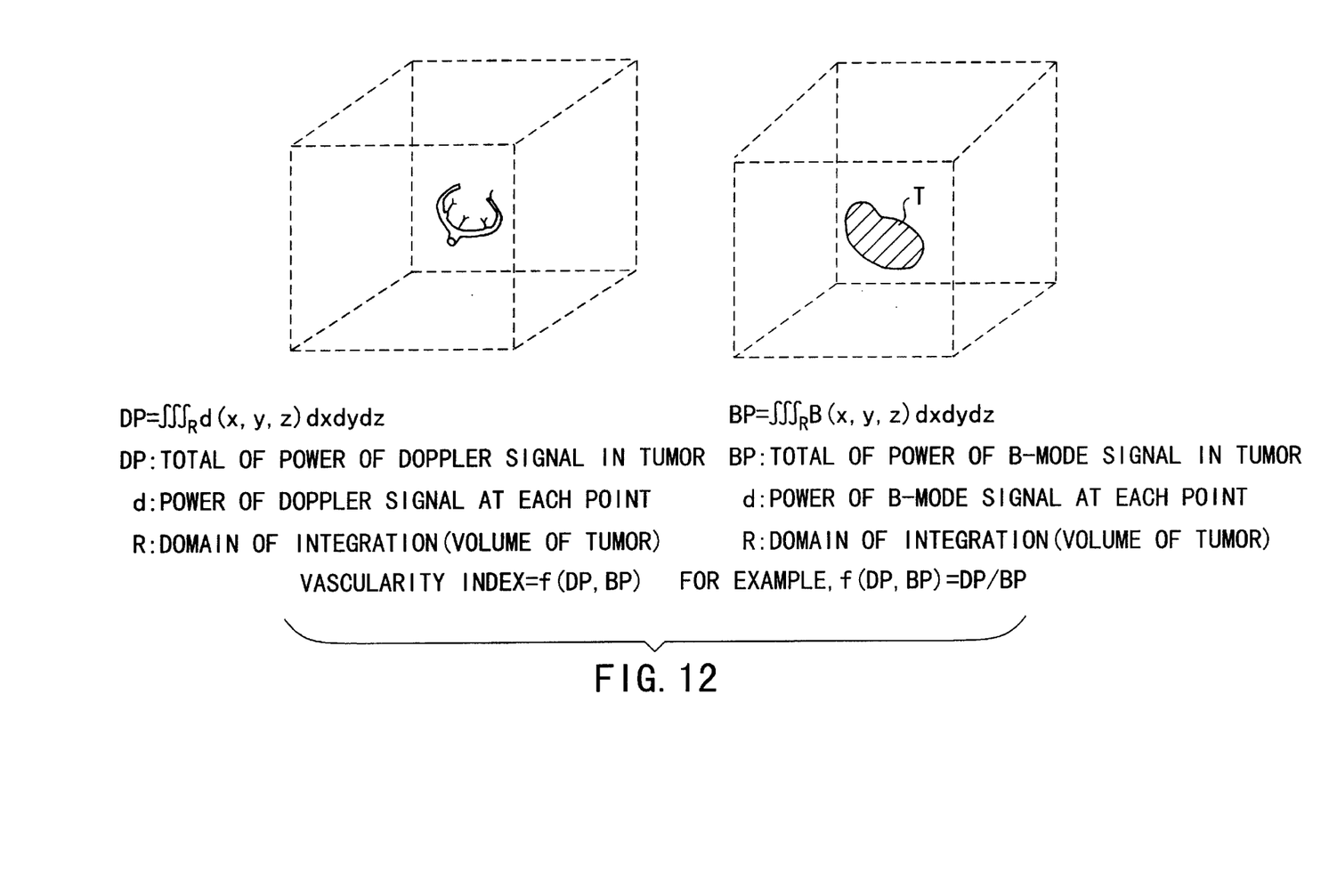
FIG. 12 is a drawing to help explain correction using the signals for a tissue image.

FIG. 12 is a drawing to help explain correction using the signal from a tissue image.

The total DP of power of a Doppler signal in a tumor is determined using the following equation:

$$DP = \int\int\int_R d(x, y, z) dx dy dz$$

where d is the power at each point of the Doppler signal and R is the extent of the tumor (or the domain of integration).

Next, the total BP of power of a B-mode signal in the tumor is determined using the following equation:

$$BP = \int\int\int_R d(x, y, z) dx dy dz$$

where d is the power at each point of the B-mode signal and R is the extent of the tumor (or the domain of integration).

Then, a vascularity index f(DP, BP) is determined to be DP/BP. On the basis of this, the transmission power and reception sensitivity of the ultrasonic probe are corrected.

While the correction signal has been obtained from the tissue image T in the tumor, a region other than the tumor may be specified as a region for correction. The intensity of the signal in a tumor can change greatly, depending on the nature of the tumor. Therefore, there may be a case where use of the correction signal from the tumor is not appropriate for correcting the transmission power or reception sensitivity.

In the case of the ultrasound diagnostic apparatus, tissue images mean generally B-mode images. Since the conditions for transmission and reception of B-mode images differ from those of color Doppler images, the effect on information to be acquired, such as attenuation, cannot be set equal. Therefore, B-mode images are not suitable for tissue images used for correction.

Figure 13:
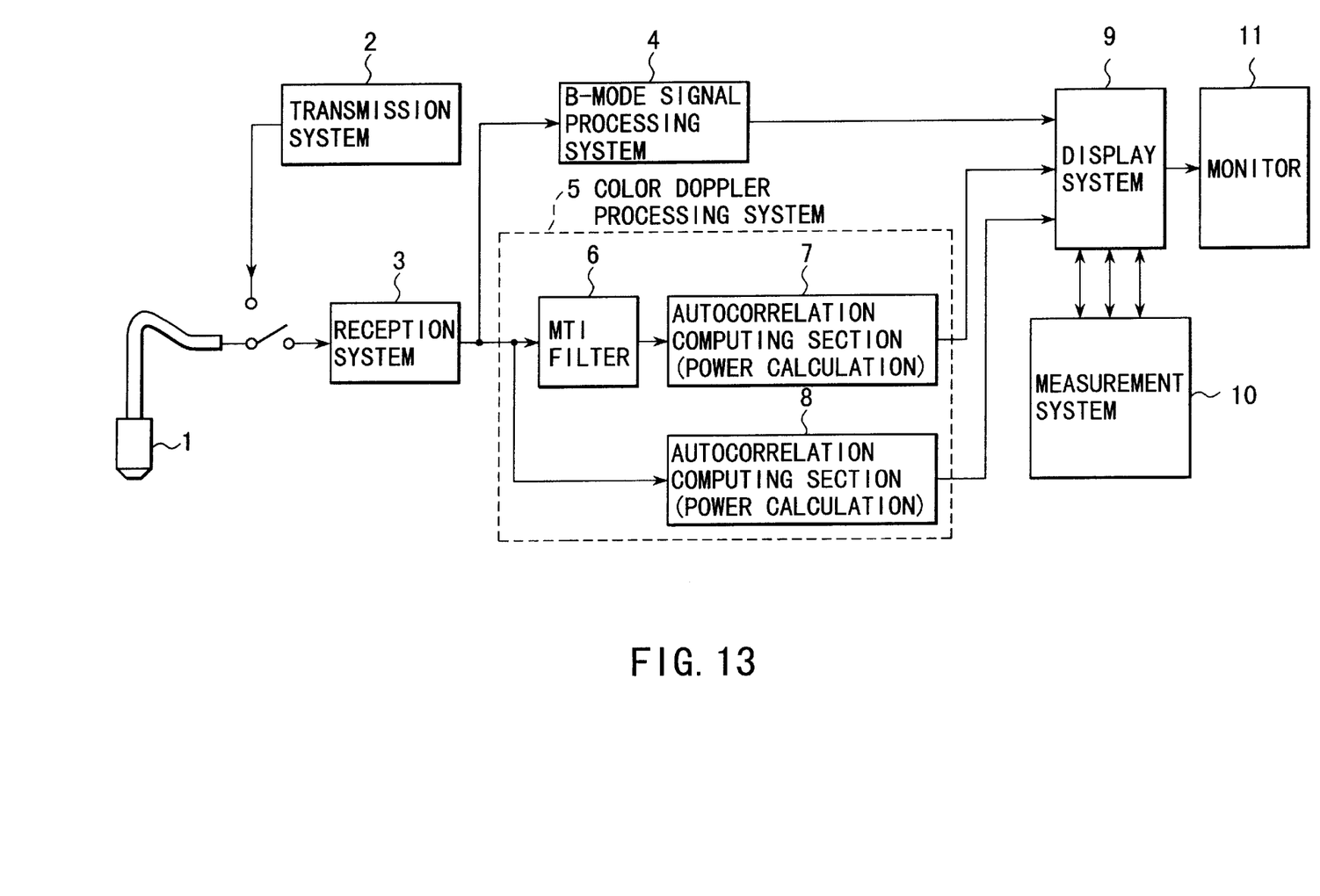
FIG. 13 is a schematic block diagram of an ultrasound diagnostic apparatus according to a third embodiment of the present invention.

FIG. 13 is a block diagram of an apparatus that solves the problem. In FIG. 13, numeral 1 indicates an ultrasonic probe, 2 a transmission system, 3 a reception system, 4 a B-mode signal processing system, 5 a color Doppler processing system, 9 a display system, 10 a measurement system, and 11 a monitor system.

The color Doppler processing system for obtaining a Doppler signal includes a HPF (high-pass filter), called an MTI filter, for removing the signal from a tissue and displaying only the signal from a bloodstream.

The color Doppler processing system 5 includes an autocorrelation computing section 7 that does power calculations after receiving a signal via the MTI filter 6 and an autocorrelation computing section 8 that does power calculations using the signal directly supplied from the reception system 3, not via the MTI filter 6.

With this configuration, a tissue image suitable for correction made for quantification can be obtained on the basis of the power value determined at the autocorrelation computing section 8.

As described above, with the third embodiment, error factors in quantification can be corrected and highly quantitative parameters be determined.

(Fourth Embodiment)

In the first to third embodiments, an ultrasonic two-dimensional tomographic image obtained by B-mode imaging (more precisely, an ultrasonic two-dimensional tomographic image concerning a single or plural cross sections viewed from a specific viewpoint) is displayed as a two-dimensional tissue image and a three-dimensional image is generated from the data acquired by color Doppler imaging and is displayed as a three-dimensional structure image. In other words, the first to third embodiments relate to a synthesis of two-dimensional image display (two-dimensional display of two-dimensional information on a subject) and three-dimensional image display (two-dimensional display of three-dimensional information on the subject).

Unlike the first to third embodiments, a fourth embodiment of the present invention synthesizes a three-dimensional tissue image with a three-dimensional blood vessel image (or structure image) and displays the resulting image.

Figure 14:
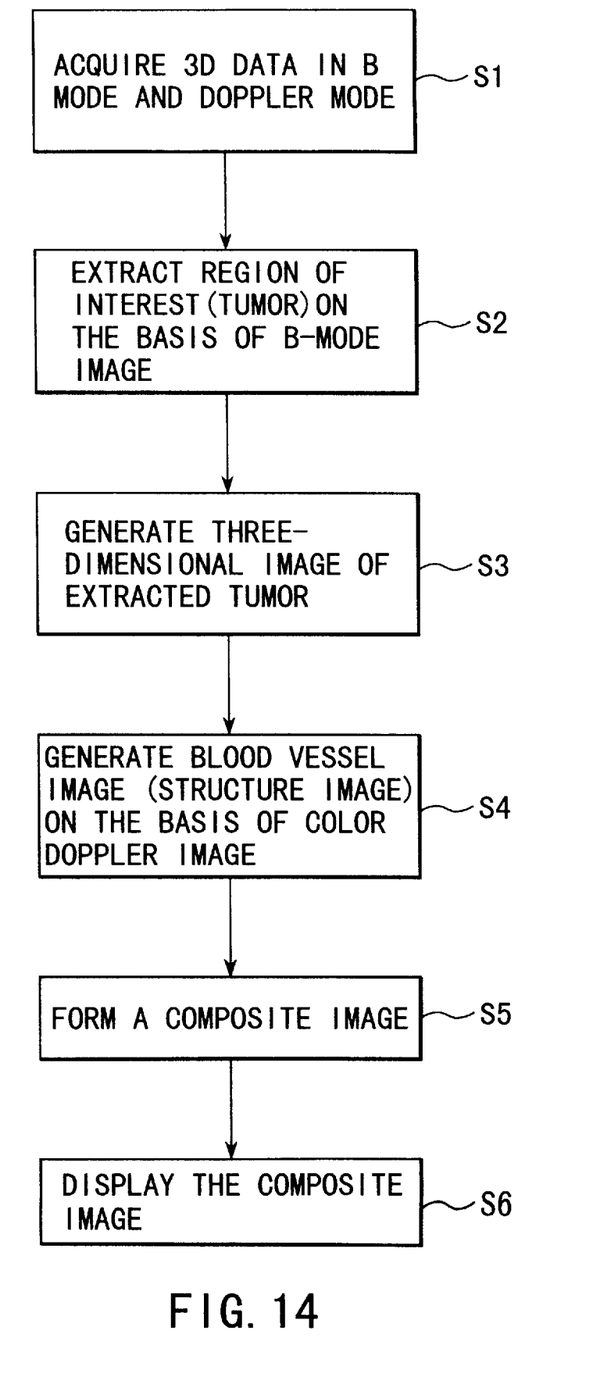
FIG. 14 is a flowchart covering the process of generating a three-dimensional tissue image and blood vessel image to the process of displaying them in an ultrasound diagnostic apparatus according to a fourth embodiment of the present invention.

FIG. 14 is a flowchart covering the process of generating a three-dimensional tissue image and blood vessel image to the process of displaying them in an ultrasound diagnostic apparatus related to the fourth embodiment of a medical image diagnostic apparatus of the present invention.

First, as shown in step S1, the ultrasound diagnostic apparatus of the fourth embodiment acquires three-dimensional data by B-mode imaging and further other three-dimensional data by color-Doppler-mode imaging carried out simultaneously with the B-mode. The B-mode imaging provides two-dimensional tomographic images and the color-Doppler-mode imaging provides bloodstream images (images representing the structure of blood vessels).

The three-dimensional data items are acquired by mechanically or manually moving a one-dimensional array ultrasonic probe in such a manner that the array fans out or by using a two-dimensional array ultrasonic probe. The three-dimensional data items (volume data items) in both of the modes correspond to each other spatially.

At step S2, for example, the tumor in the internal organ parenchyma is extracted as a region of interest from the two-dimensional tomographic images obtained by the B-mode imaging. Then, a three-dimensional tumor image (or tissue image) is generated by subjecting the extracted tumor image to three-dimensional image processing composed of volume rendering (step S3). Of course, an object to be extracted from the tissue image is not limited to a tumor image.

Next, at step S4, a three-dimensional blood vessel image (or a structure image) is generated by subjecting the bloodstream images (or the images representing the structure of blood vessels) obtained by the color-Doppler-mode imaging to three-dimensional image processing composed of volume rendering. The process of generating a tumor image at steps S2 and S3 may be carried out in sequence as described above or be performed in parallel.

Then, at step S5, the three-dimensional tissue image and blood vessel image are synthesized. At this step, a specific viewpoint is set and the light source is tracked from the viewpoint. Then, both the images are synthesized in the process of setting the transmittance of voxels in each image according to the positional relationship between the tumor image and blood vessel image.

Figure 15A:
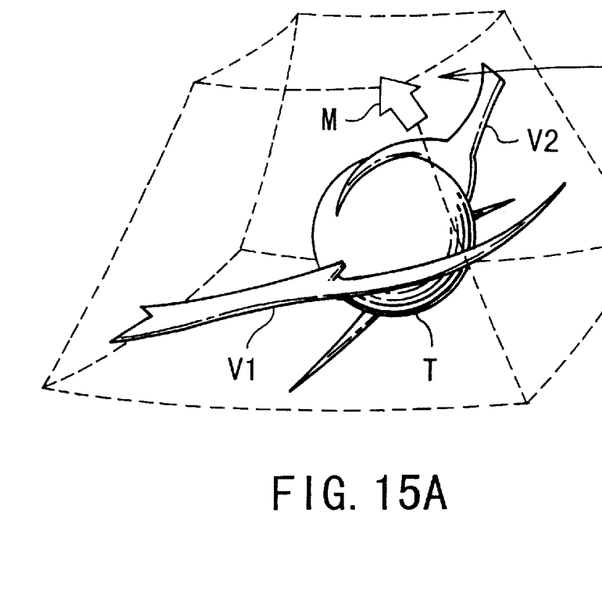
FIG. 15A shows an example of displaying a composite image from a specific viewpoint.

Then, the synthesized image at step S5 is displayed at step S6. FIG. 15A shows a display example of the composite image from a specific viewpoint. In FIG. 15A, T indicates a three-dimensional image of a tumor and V1 and V2 represent a three-dimensional blood vessel image.

Figure 15B:
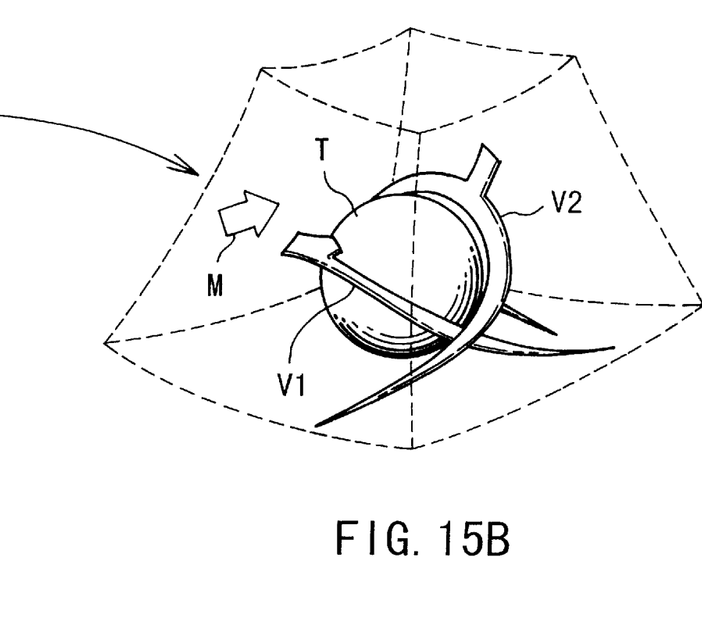
FIG. 15B shows an example of displaying a composite image from another viewpoint.

Furthermore, M indicates a marker for setting a viewpoint. Specifically, at step S6, the operator can change the viewpoint by manipulating the marker M. When the operator has changed the viewpoint, the parameter for the viewpoint is changed, the processes at step S2 to step S5 are repeated, and the contents of the display are updated. FIG. 15B shows a display example when the viewpoint has been changed.

According to the fourth embodiment, the positional relationship between the tumor and blood vessels represented in the tissue image can be observed accurately.

As described above, with the present invention, it is possible to provide the following medical image diagnostic apparatuses:

(1) A medical image diagnostic apparatus which displays an image of a network structure, such as blood vessels, and an image of tissue with gradation, such as parenchymatous internal organs, in such a manner that their positional relationship can be observed accurately.

(2) A medical image diagnostic apparatus capable of obtaining quantitative parameters accurately from three-dimensional information on an image of tissue and on an image of a structure, such as blood vessels.

Additional advantages and modifications will readily occurs to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A medical image diagnostic apparatus comprising:
   acquisition means for acquiring first three-dimensional image data in a first-imaging mode and further acquiring second three-dimensional image data in a second imaging mode in such a manner that the positional coordinates of said second three-dimensional image data correspond to those of said first three-dimensional image data;
   tomographic image generation means for generating an ultrasonic tomographic image from said first three-dimensional image data acquired by said acquisition means;
   three-dimensional image generation means for generating a three-dimensional image from said second three-dimensional image data acquired by said acquisition means;
   position changing means for changing a position of the ultrasonic tomographic image generated by said tomographic image generation means;
   synthesizing means for synthesizing the ultrasonic tomographic image generated by said tomographic image generation means with the three-dimensional image generated by said three-dimensional image generation means in such a manner that the position of the ultrasonic tomographic image is caused to match with the three-dimensional image; and
   display means for displaying the synthesized image from said synthesizing means.

2. A medical image diagnostic apparatus according to claim 1, wherein at least one of said first and second three-dimensional image data is ultrasonic image data.

3. A medical image diagnostic apparatus according to claim 1, wherein said first imaging mode is a B-mode of an ultrasound diagnostic apparatus and the tomographic image generated by said tomographic image generation means is a B-mode image.

4. A medical image diagnostic apparatus according to claim 1, wherein said second imaging mode is a Doppler mode of an ultrasound diagnostic apparatus and the three-dimensional image generated by said three-dimensional image generation means is a Doppler-mode image.

5. A medical image diagnostic apparatus according to claim 1, wherein the tomographic image generated by said tomographic image generation means is a tissue image representing the parenchyma of internal organs of a subject.

6. A medical image diagnostic apparatus according to claim 1, wherein the three-dimensional image generated by said three-dimensional image generation means is a structure image representing a bloodstream in a subject.

7. A medical image diagnostic apparatus comprising:

acquisition means for acquiring first three-dimensional image data in a first imaging mode and further acquiring second three-dimensional image data in a second imaging mode in such a manner that the positional coordinates of said second three-dimensional image data correspond to those of said first three-dimensional image data;

tomographic image generation means for generating an ultrasonic tomographic image from said first three-dimensional image data acquired by said acquisition means;

three-dimensional image generation means for generating a three-dimensional image from said second three-dimensional image data acquired by said acquisition means;

position changing means for changing a position of the ultrasonic tomographic image generated by said tomographic image generation means;

region setting means for setting a specific region in the three-dimensional image generated by said three-dimensional image generation means on the basis of the ultrasonic tomographic image generated by said tomographic generation means; and calculation means for calculating living organism information on a subject on the basis of data on the specific region set by said region setting means of the three-dimensional image data acquired in said second imaging mode.

8. A medical image diagnostic apparatus according to claim 7, wherein at least one of said first and second three-dimensional image data is ultrasonic image data.

9. A medical image diagnostic apparatus according to claim 7, wherein said first imaging mode is a B-mode of an ultrasound diagnostic apparatus and the tomographic image generated by said tomographic image generation means is a B-mode image.

10. A medical image diagnostic apparatus according to claim 7, wherein said second imaging mode is a Doppler mode of an ultrasound diagnostic apparatus and the three-dimensional image generated by said three-dimensional image generation means is a Doppler-mode image.

11. A medical image diagnostic apparatus according to claim 7, wherein the tomographic image generated by said tomographic image generation means is a tissue image representing the parenchyma of internal organs of a subject.

12. A medical image diagnostic apparatus according to claim 7, wherein the three-dimensional image generated by said three-dimensional image generation means is a structure image representing a bloodstream in a subject.

13. A medical image diagnostic apparatus comprising:

acquisition means for acquiring first three-dimensional image data in a first imaging mode and further acquiring second three-dimensional image data in a second imaging mode in such a manner that the positional coordinates of said second three-dimensional image data correspond to those of said first three-dimensional image data;

generation means for generating ultrasonic image data on a three-dimensional region from said first three-dimensional image data acquired by said acquisition means;

three-dimensional image generation means for generating a three-dimensional image from said second three-dimensional image data acquired by said acquisition means;

position changing means for changing a position of the three-dimensional image generated by said generation means;

synthesizing means for synthesizing the first three-dimensional image with the second three-dimensional image in such a manner that the position of the first three-dimensional image is caused to match with that of the second three-dimensional image; and display means for displaying the composite image from said synthesizing means.

14. A medical image diagnostic apparatus according to claim 13, wherein at least one of said first and second three-dimensional image data is ultrasonic image data.

15. A medical image diagnostic apparatus according to claim 13, wherein said first imaging mode is a B-mode of an ultrasound diagnostic apparatus and said first generation means generates a B-mode three-dimensional image.

16. A medical image diagnostic apparatus according to claim 13, wherein said second imaging mode is a Doppler mode of an ultrasound diagnostic apparatus and said second generation means generates a Doppler-mode three-dimensional image.

17. A medical image diagnostic apparatus according to claim 13, wherein the first three-dimensional image generated by said first generation means is a tissue image representing the parenchyma of internal organs of a subject.

18. A medical image diagnostic apparatus according to claim 13, wherein the second three-dimensional image generated by said second generation means is a structure image representing a bloodstream in a subject.

19. A medical image diagnostic apparatus comprising:

a first memory for storing three-dimensional image data acquired in a first imaging mode;

a second memory for storing three-dimensional image data acquired in a second imaging mode, which is different from the first imaging mode;

extracting means for extracting data on a partial region from the three-dimensional image data stored in the first memory;

image processing means for producing a display image by synthesizing extracted image data acquired in the first imaging mode, with the three-dimensional image data acquired in the second imaging mode, such that the extracted image data and the three-dimensional image data are matched in position;

means for displaying the display image; and means for changing a position where data are extracted by the extracting means.

20. A medical image diagnostic apparatus comprising:

a first memory for storing three-dimensional image data acquired in a first imaging mode;

second memory for storing three-dimensional image data acquired in a second imaging mode which is different from the first imaging mode;

data processing means for extracting data on a cross section from the three-dimensional image data stored in the first memory;

region setting means for setting a region for quantification on the basis of image data on said cross section obtained by the data processing means;

display means for displaying the image data on the cross section together with lines indicating the region for quantification; and calculation means for calculating information on a living body on the basis of data which is extracted from the three-dimensional image data acquired in the second imaging mode and which corresponds to the region for quantification.

21. A medical image processing method comprising the steps of:

acquiring ultrasonic data in a first imaging mode, so as to obtain ultrasonic image data regarding a cross section;

acquiring ultrasonic data in a second imaging mode different from the first imaging mode, so as to obtain ultrasonic image data regarding a three-dimensional region;

synthesizing the ultrasonic image data acquired in the first imaging mode and pertaining to the cross section with the ultrasonic image data acquired in the second imaging mode and pertaining to the three-dimensional region, such that data synthesis is executed in a position-matched state, thereby obtaining a display image;

displaying the display image; and changing a position of the cross section.

22. A medical image processing method comprising the steps of:

acquiring three-dimensional image data in a first imaging mode and a second imaging mode, which are different from each other;

producing an ultrasonic image of a partial three-dimensional region from the three-dimensional image data acquired in the first imaging mode;

changing a position of the three-dimensional region produced in the producing step such that a first three-dimensional image obtained in the first imaging mode is changed related to a second three-dimensional image obtained in the second imaging mode;

synthesizing the first three-dimensional image and the second three-dimensional image together in a position-matched state; and displaying an image obtained in the synthesizing step.

23. A medical image processing method comprising the steps of:

acquiring ultrasonic data in a first imaging mode so as to obtain ultrasonic image data on a cross section;

acquiring ultrasonic data in a second imaging mode different from the first imaging mode, so as to obtain ultrasonic image data regarding a three-dimensional region;

determining a region for quantification on the basis of the image data on the cross section;

displaying the image data on the cross section together with lines indicating the region for quantification; and calculating information on a living body on the basis of data which is extracted from the three-dimensional image data acquired in the second imaging mode and which corresponds to the region for quantification.

\* \* \* \* \*